(12) United States Patent
Muller et al.

(10) Patent No.: US 7,634,050 B2
(45) Date of Patent: Dec. 15, 2009

(54) MAMMOGRAPHY DEVICES

(75) Inventors: Serge Muller, Guyancourt (FR); Aurelie Roncaglioni, Bois d'Arcy (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/271,957

(22) Filed: Nov. 17, 2008

(65) Prior Publication Data
US 2009/0135996 A1 May 28, 2009

(30) Foreign Application Priority Data
Nov. 23, 2007 (FR) .................................. 07 59281

(51) Int. Cl.
*A61B 6/04* (2006.01)
(52) U.S. Cl. ........................................ 378/37; 378/196
(58) Field of Classification Search ............ 378/37, 378/193–198
See application file for complete search history.

(56) References Cited

U.S. PATENT DOCUMENTS

| 4,926,453 A | 5/1990 | Toniolo | 378/37 |
| 4,979,196 A | 12/1990 | Lietaud | 378/37 |
| 6,298,114 B1 | 10/2001 | Yoda | |

FOREIGN PATENT DOCUMENTS

| DE | 102006038063 A1 | 3/2007 |
| DE | 102006004590 A1 | 8/2007 |
| EP | 0332519 A1 | 9/1989 |
| EP | 0387956 A1 | 9/1990 |
| EP | 0461028 A1 | 12/1991 |
| WO | WO01/66013 A2 | 9/2001 |
| WO | WO03/041586 A1 | 5/2003 |

*Primary Examiner*—Courtney Thomas
(74) *Attorney, Agent, or Firm*—Global Patent Operation; Jonathan E. Thomas

(57) ABSTRACT

A mammography device comprising at least one X-ray source, a C-arm which supports said source, as well as a console which integrates an X-ray detector, wherein the C-arm and the console are movable relative to one another. The wherein C-arm and the console are mechanically decoupled from one another so that the C-arm and/or the console are movable relative to one another, between an exposure-taking position where the C-arm is in an immediate vicinity of the console, and a position wherein the C-arm and the console are separated from one another and wherein access to said C-arm and/or to said console is facilitated.

10 Claims, 6 Drawing Sheets

MAMMOGRAPHY DEVICES

CROSS-REFERENCE TO RELATED APPLICATIONS

This application claims priority under 35 U.S.C. §119(a)-(d) to prior-filed, co-pending French patent application serial number 0759281, filed on Nov. 23, 2007, which is hereby incorporated by reference in its entirety.

FIELD OF THE INVENTION

The field of the invention relates to medical imaging and, more particularly, to mammography devices.

BACKGROUND OF THE INVENTION

Mammography devices conventionally comprise at least one X-ray source and a console which is arranged opposite said source and intended to receive and support the patient's breast. This console integrates a detector for detecting the X-rays after they have passed through the patient's breast (array of sensors, X-ray sensitive film cassette, etc.) and, where applicable, is associated with compression means, typically a plate (also referred to as a breast compression paddle), which is designed to compress the breast against the console when images are being taken.

Mammography devices of this type are, for example, those proposed by the GE Medical Systems company under the name of "Senographe" (registered trademark). A detailed example of the structure of such a device is also described in the patent U.S. Pat. No. 4,979,196.

The console is conventionally held by the support (arc of a circle) on which the X-ray source moves about in order to scan the various desired angles of view.

SUMMARY OF THE INVENTION

Even though devices of the type just mentioned already enable practitioners to have a certain degree of access to the patient's breast, it is desired, however, for this access to be further improved.

Embodiments of the invention address at least this set of problems.

For example, one embodiment of the invention provides a device which is capable of being used both for analyses with the patient standing or sitting in front of the device and for analyses with the patient in a recumbent position.

More particularly, an embodiment of the invention provides a mammography device that includes:

at least one X-ray source, a C-arm which supports said source, and a console which integrates an X-ray detector, wherein the C-arm and the console are movable relative to one another.

In particular, the C-arm and console are mechanically decoupled from one another. The C-arm and/or the console are movable relative to one another, between an exposure-taking position wherein the C-arm is in the immediate vicinity of the console, and a position wherein the C-arm and the console are separated from one another and wherein access to said C-arm and/or to said console is facilitated.

Thus, it is possible to separate the C-arm and the console from one another in order to enable complete access to the patient's breast, before or after taking exposures, in order to position it or so as to operate and/or carry out or control preliminary steps, e.g., such as the injection of a contrasting liquid and/or subsequent steps, e.g., such as a biopsy.

An embodiment of the invention also provides a mammography device that includes:

at least one X-ray source, a C-arm which supports said source, and a console which integrates an X-ray detector, wherein the console and the C-arm are mounted rotatably about axes perpendicular to the major axis of the C-arm, in order to enable the inclination and/or tilting of the C-arm and the console.

In particular, for example, the C-arm can be tilted into a horizontal position, while the console can be tilted into a vertical position.

A device such as this can thus be used both with a patient in seated or standing position and with a patient in an inclined or else recumbent position.

BRIEF DESCRIPTION OF THE DRAWINGS

Other characteristics and advantages of embodiments of the invention will become further apparent from the following description, which is purely illustrative and non-limiting, and which should be read with reference to the appended Figures, in which.

DETAILED DESCRIPTION OF THE INVENTION

Figure 1:
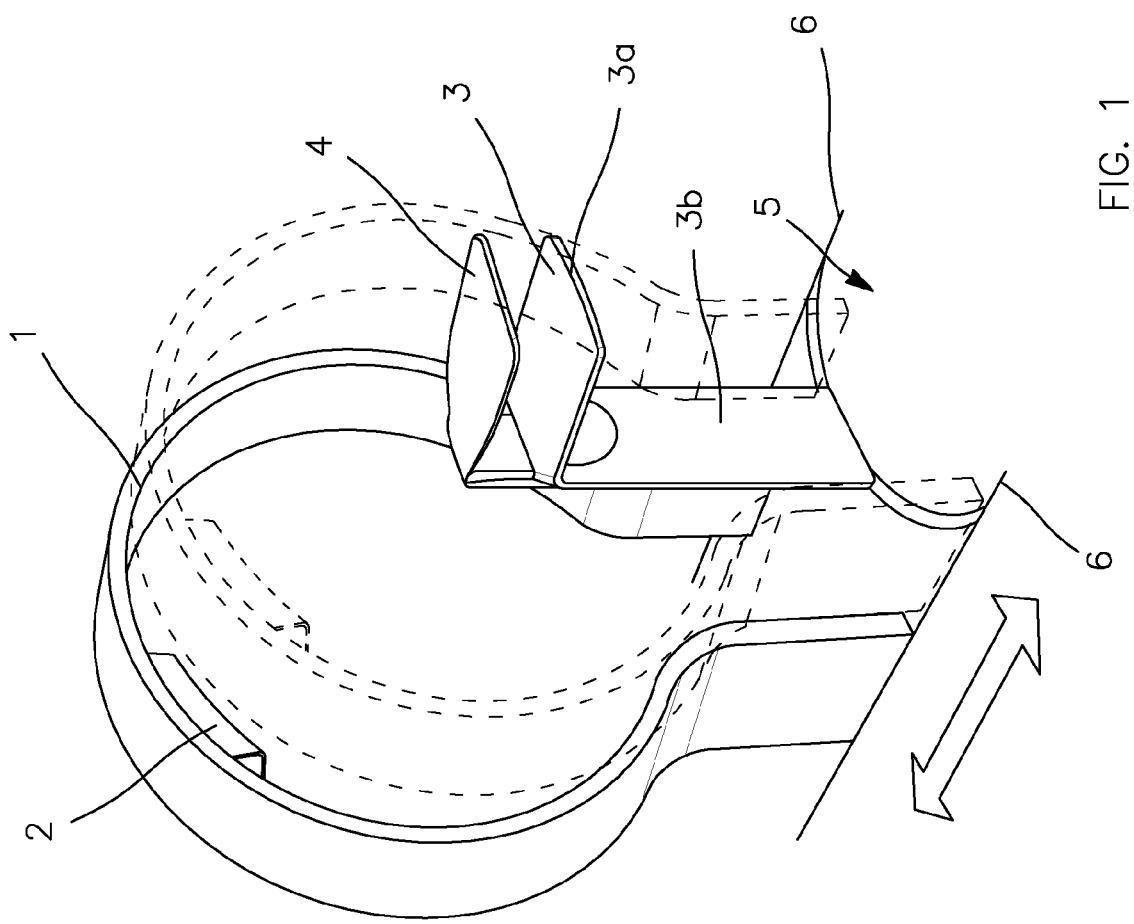
FIG. 1 is a perspective schematic representation of a device according to one possible embodiment of the invention.

The device shown in FIG. 1 includes an arc-of-circle shaped support 1 or C-arm holding at least one X-ray source 2.

The source 2 can consist of one or several sources held by the C-arm and movable along the C-arm. In another embodiment, it can be provided with a plurality of stationary primary sources distributed along the C-arm 1.

The device of FIG. 1 also comprises a console 3 into which the detector 3a of the device is integrated (array of sensors, X-ray sensitive film cassette, etc.).

A movable compression plate 4 (or paddle) is added on to the console above the console and makes it possible to ensure compression of the breast. This plate 4 is made of an X-ray transparent material, and is of the type described in the patent application WO 03/041586, for example.

The arc-of-circle shaped support 1, the console 3 and the compression plate 4 thereof are mounted on a platform 5.

In the example of FIG. 1, and as shown by the double arrow in this Figure, the support 1 is capable of sliding over this platform 5, parallel to a plane which appears to pass through the axis of said arc-of-circle shaped support 1 and appears to be perpendicular to the plane of the console 3, and to thus be separated from or brought closer to the console 3. As for the console 3, it is held by a leg, for example, which is stationary in relation to the platform 5, or else movable in translation as well as in rotation, in order to facilitate access, for example, to the various hardware elements, during maintenance of the equipment.

Thus, the arc-of-circle shaped support 1 can be moved between at least two positions:

one in which the C-arm 1 is substantially plumb over the console, in order to enable acquisition of the images; the C-arm 1 then at least partially overlaps the console 3 and the X-rays emitted by the source 2 intercept the patient's breast and the detector 3a; and another, in which the C-arm is sufficiently distant from the console 3 to enable a free passageway for the practitioner around the patient and the console.

The C-arm 1 and the console 3 are thus decoupled from one another.

The X-ray source 2 and the console 3 are no longer mechanically linked on the same access mechanism.

To illustrate, in order to enable this relative movement of the C-arm 1 in relation to the console 3, it is possible to (non-limitatively) provide for the bases of the C-arm 1 to include one or more carriages (not shown) cooperating with rails 6 arranged on the platform 5.

Figure 6:
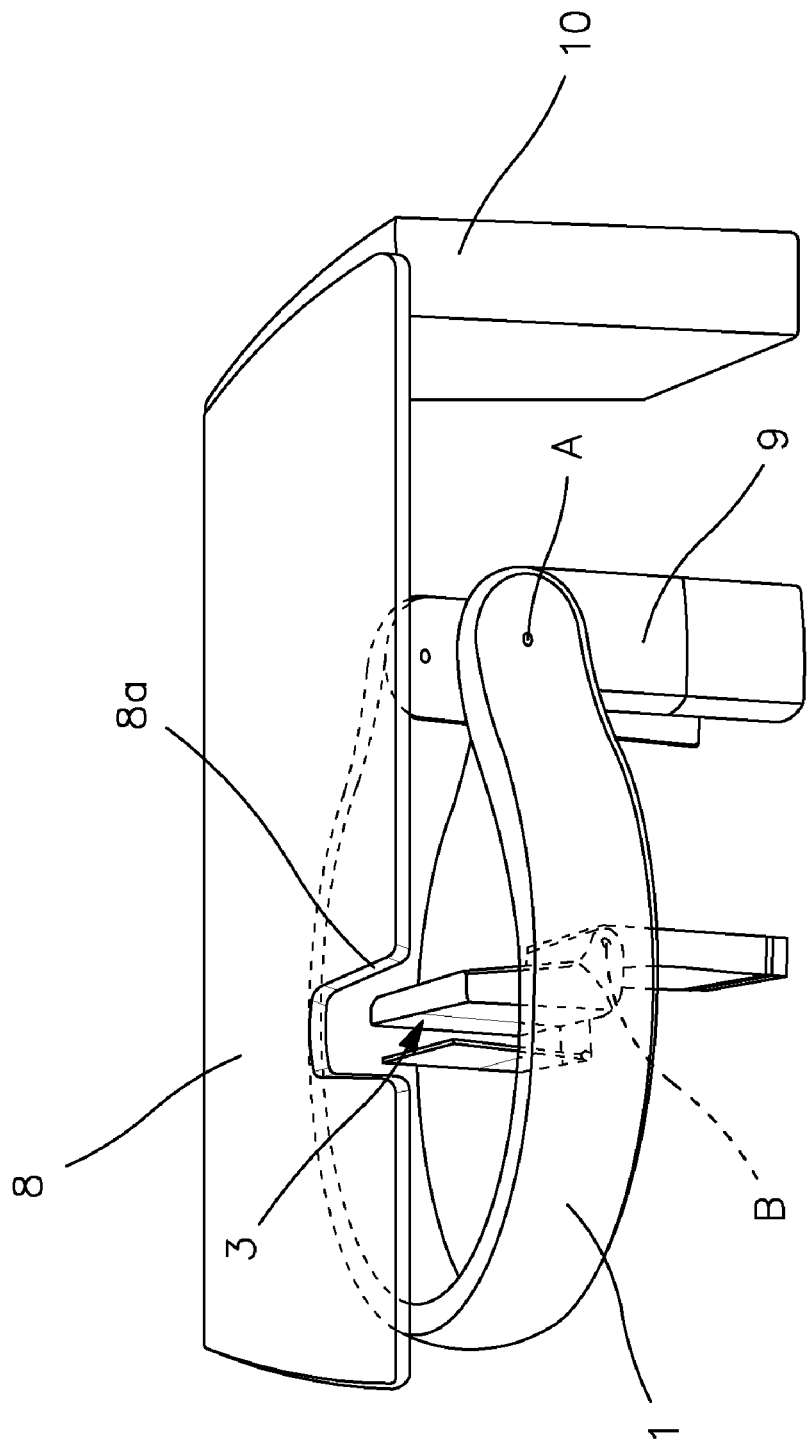
FIG. 6 is a perspective schematic representation showing another possible embodiment of the invention.

The rails 6 can run on both sides of the console, enabling the C-arm to assume extreme positions distant from and in front of the console, or distant from and behind the console, and all of the intermediate positions between these two extreme positions. FIGS. 1 and 6 show what is meant in this document by in front of or behind the console: in FIG. 1, the bases of the C-arm are in front of the console, and in FIG. 6, the bases of the C-arm are behind the console.

In another embodiment not shown, the C-arm is provided with a caster rolling on the platform, and a spatial location device enabling it to be located in relation to the console.

The X-ray source 2 and the console 3 are no longer mechanically linked and are geometrically mapped by means of the rails or any other means which could be attached to each of these two elements and which would make it possible to know the relative position of the X-ray source 2 in relation to the console 3 or vice versa.

A means such as this could be a GPS or navigation-type system with a known reference point situated in the room where the device is installed and with which geometric calibration is ensured for each of the two elements (tube and console), which would then make it possible to do without the rails restricting the freedom of movement of one element in relation to the other, and to obtain a true mechanical decoupling of these two elements.

Movement is motorised and/or controllable or, where appropriate, unassisted (manual).

Figure 2:
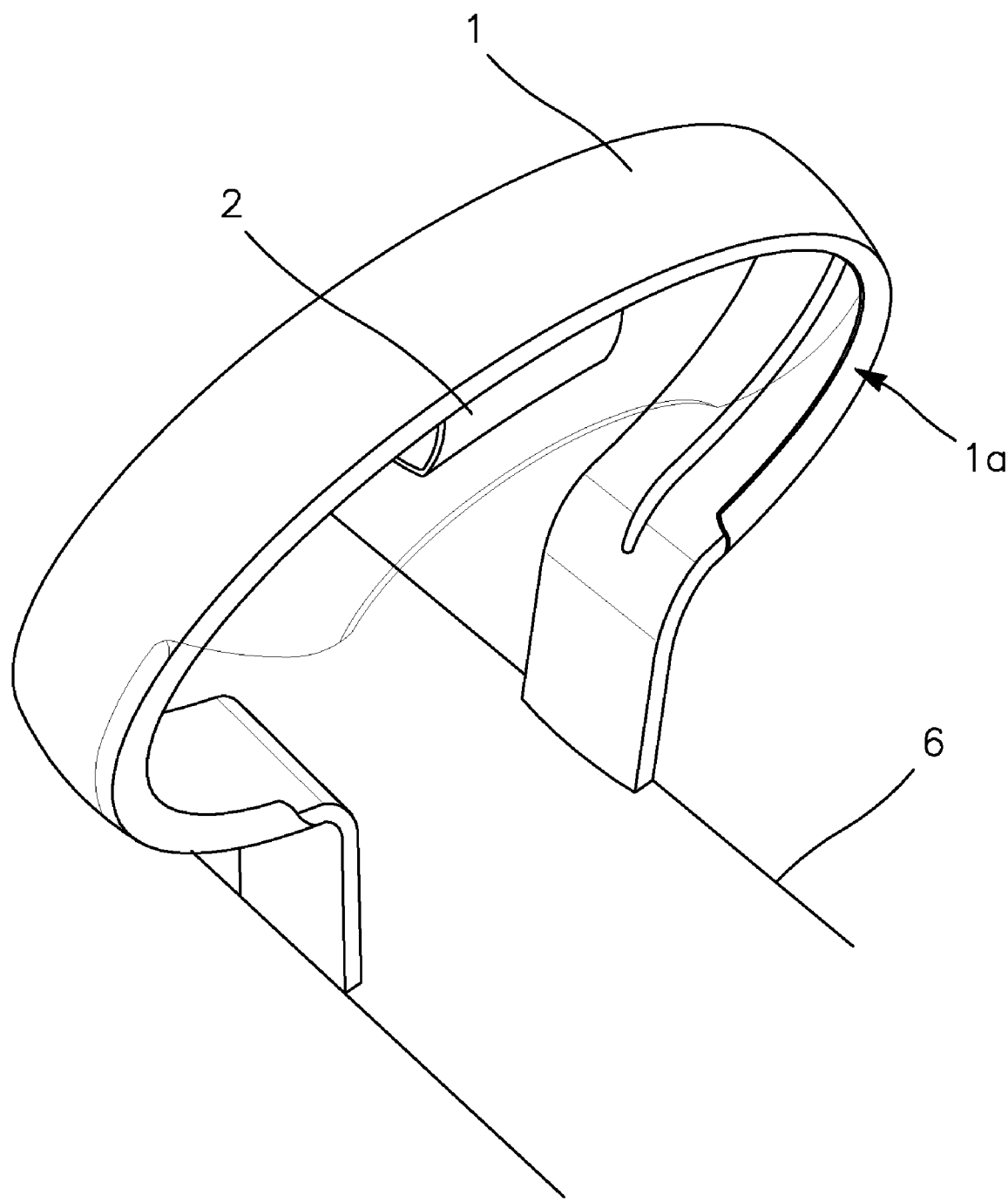
FIG. 2 is a perspective schematic representation of the C-arm of the device of FIG. 1.

For example, as illustrated in FIG. 2, the C-arm 1 can include an outside rim 1a forming a handle, which enables the operator to grasp onto it in order to manually move said C-arm 1 by sliding it along the rails 6 thereof.

In another embodiment, it can be anticipated for the console and the patient to be movable and for the C-arm to remain stationary (MRI or CAT type).

In another embodiment, the console and the C-arm can both be movable in relation to the platform 5.

The platform 5 can also be a platform which integrates a certain number of electronic components, such as, but not limited to data cables and/or drive cables and/or power cables between the console 3 and the C-arm 1 and/or between the device and the exterior components, e.g., such as the electrical power supply, the remote-control station, the display and/or information storage devices, X-ray generator, system component temperature control system, etc.

Figure 3:
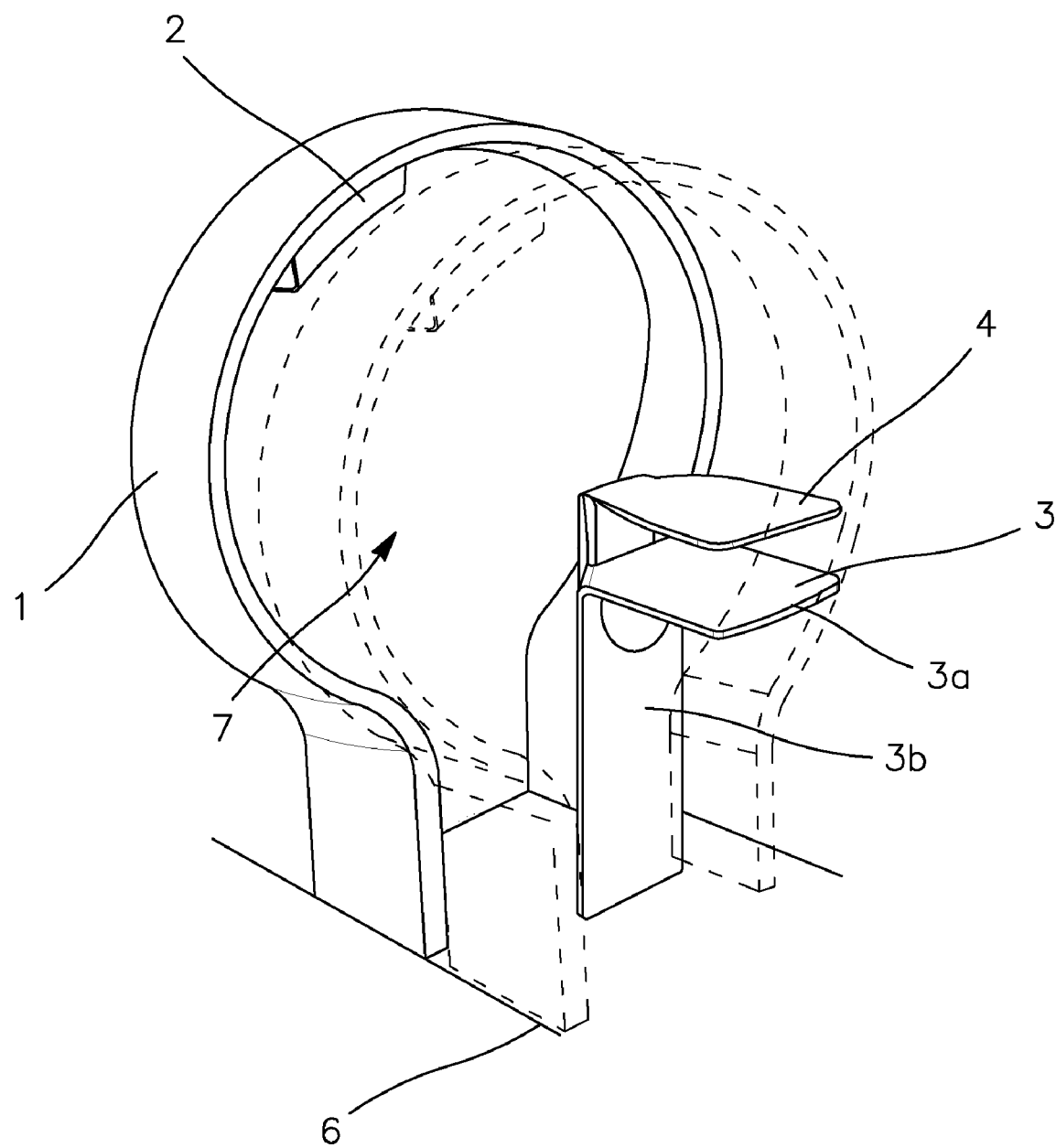
FIG. 3 shows a possible alternative embodiment for the device of FIG. 1.

Furthermore, in one embodiment, and as shown in FIG. 3, a radiation shield 7 is integrated into the bottom of the C-arm 1, on the side opposite the patient, in the form of an X-ray transparent and impermeable surface.

Figure 5:
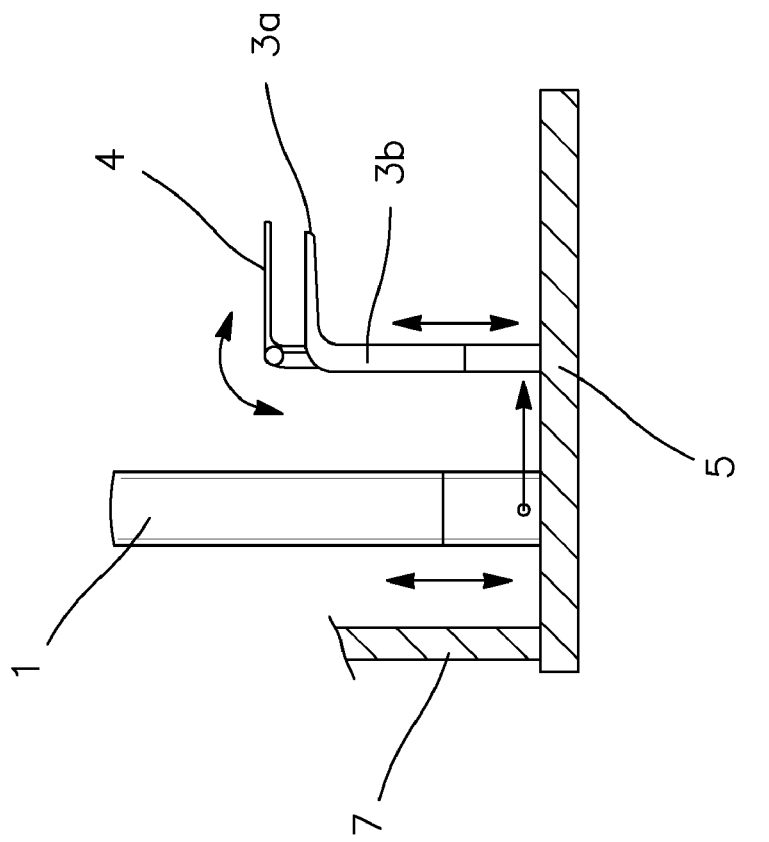
FIG. 5 is a cross-sectional schematic representation of the device of FIG. 3.
Figure 4:
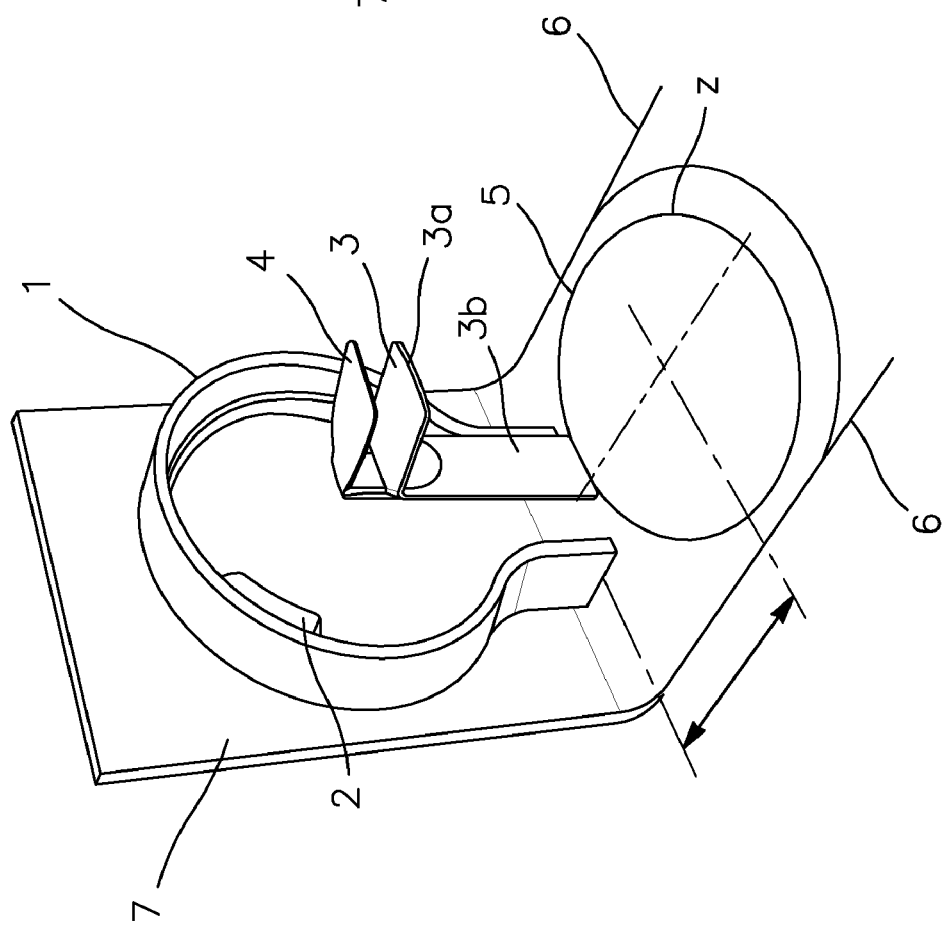
FIG. 4 shows another possible alternative embodiment.

Alternatively, and as shown in FIGS. 4 and 5, the shield 7 can be separate from the C-arm 1 and be integral with the platform 5 or attached thereto.

In FIG. 4, the area Z is also shown where the patient is intended to be, in standing position or in sitting position on a chair (no shown), in front of the console 3.

As shown in FIG. 5, the console 3 is either a manually or power-driven height-adjustable console. The compression paddle or plate is itself also adjustable manually or in a power-driven and/or controllable manner. The compression paddle and the console 3 which integrates the detector can rotate about an axis in order to enable the acquisition of breast images at various projections.

As shown in FIG. 6, the C-arm 1 and the assembly consisting of the console 3 and the compression paddle 4, thereof can be pivotably mounted around two axes of rotation referenced in FIG. 6 as A and B, respectively.

Thus, other degrees of freedom can be added to the device, in particular to allow the C-arm as well as the detector/compression system to be inclined in such a way that the latter remains substantially perpendicular to the plane of the C-arm. By adding the capability of varying the height of the C-arm (e.g., with telescoping legs 9) it is thereby possible to bring the C-arm into the horizontal position and the detector/compression system assembly into the vertical position, in order to use the system with the patient in the stomach-down position on a table 8 through which the breast passes.

The table 8 is either an exterior element which is put into position once the C-arm and the console 3 have been tilted, or an element integrated into the platform 5, behind the console, and comprising a base 10 and a plate 8 that is pivotable in relation to the base 10, between a vertical storage position, and a horizontal operating position. The base 10 can be movable in relation to the platform. A cut-out 8a, e.g., lateral, and more typically through the table, is made in said table in order to enable positioning of the patient's breast and the placement thereof on the console 3.

Figure 7A:
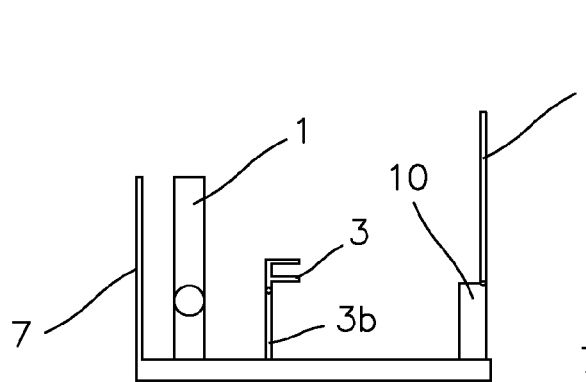
FIGS. 7a to 7d show various possible operating configurations for a mammography device in accordance with the embodiments of the preceding figures.
Figure 7B:
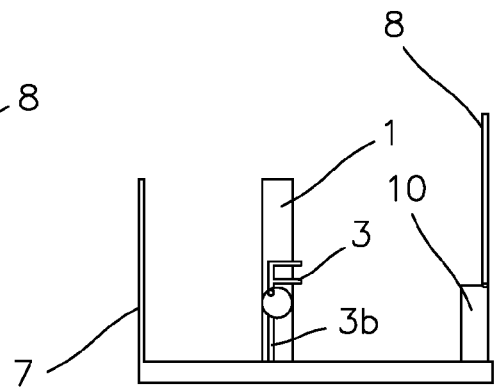
Figure 7C:
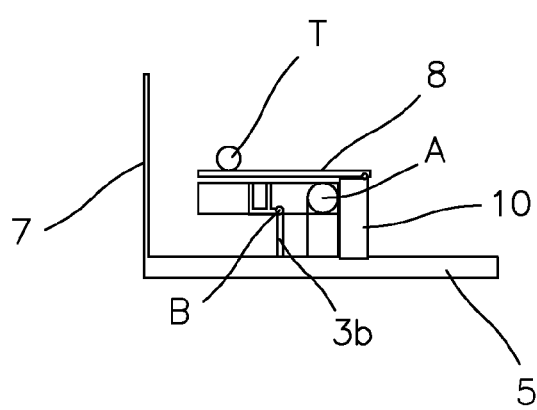

In the case shown in FIG. 6, the console 3 is stationary in relation to the platform 5, and it is therefore necessary for the C-arm to be able to shift into a position behind the console before bringing it into a horizontal position. This is what is shown in FIGS. 7a to 7c. Starting from the position shown in FIG. 7a, the C-arm is moved into its position in FIG. 7b (which corresponds to the exposure-taking position), and then beyond, until the table 8 is placed in position, the console 3 being tilted to assume a vertical position, and then the C-arm itself being tilted to assume its horizontal position. The patient can then lie down with her head T on its side, as shown schematically in FIG. 7c.

Figure 7D:
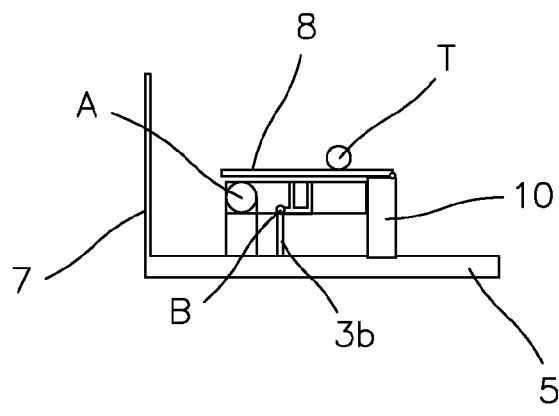

In one embodiment (see FIG. 7d), the leg 3b of the console 3 is movable in rotation about a vertical axis, by way of non-limiting example, passing through a centre point of the detector, making it possible to pivot the console 180° in order to shift it from its position shown in FIG. 7c to its position shown in FIG. 7d. In this case, it is no longer necessary to shift the C-arm into position behind the console prior to bringing it into horizontal position. This embodiment makes it possible to do without rails on each side of the console.

In this embodiment, the patient is lying down on the table with her head towards the rear, whereas in the representation of FIG. 6, she is lying down on the table with her head towards the front.

Finally, the mammography device just described is capable of implementing all of the operational functions and characteristics of a mammography device of the prior art, whether it be for taking exposures, compressing the breast, biopsy procedures, with the possible use of optional components already known in the prior art, e.g., such as automated, semi-automated or manual biopsy guns and/or automated, semi-automated or manual devices for injecting contrast media.

It has the further advantage of improving the accessibility of the practitioner or operator to the patient's breast or to the patient herself.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the scope of the following claims.

The invention claimed is:

1. A mammography device, comprising:
    an X-ray source;
    a C-arm which supports said X-ray source; and
    a console which integrates an X-ray detector,
    wherein the C-arm and/or the console are movable relative to one another.

2. The mammography device of claim 1,
    wherein the C-arm and the console are mechanically decoupled from one another, and
    wherein the C-arm and/or the console are movable relative to one another between an exposure-taking position where the C-arm is in an immediate vicinity of the console and a position where the C-arm and the console are separated from one another and access to said C-arm and/or to said console is facilitated.

3. The mammography device of claim 1, wherein the C-arm and the console are mounted on a platform, and one and/or the other of said C-arm and said console are configured to be moved about thereon.

4. The mammography device of claim 1, wherein the platform is a raised platform which integrates electronic components, in particular cables.

5. The mammography device of claim 1, wherein the C-arm is mounted on guide rails integrated into the platform.

6. The mammography device of claim 1, further comprising:
    a bottom which consists of a radiation shield integrated into the C-arm.

7. The mammography device of claim 3, further comprising:
    a stationary radiation shield held by the platform and separate from the C-arm which slides thereon.

8. The mammography device of claim 1, wherein at least one of the console and the C-arm is height-adjustable.

9. The mammography device of claim 1, wherein the console and the C-arm are rotatably mounted around axes perpendicular to a major axis of the C-arm, to enable the inclination and/or tilting of the C-arm and the console.

10. The mammography device of claim 1, further comprising:
    a table configured be added onto said device when the C-arm and the console are in a tilted position.

* * * * *